US006669961B2

(12) United States Patent
Kim et al.

(10) Patent No.: US 6,669,961 B2
(45) Date of Patent: Dec. 30, 2003

(54) MICROPARTICLES

(75) Inventors: Kyekyoon Kim, Champaign, IL (US); Daniel W. Pack, Champaign, IL (US); Cory Berkland, Urbana, IL (US)

(73) Assignee: Board of Trustees of University of Illinois, Urbana, IL (US)

( * ) Notice: Subject to any disclaimer, the term of this patent is extended or adjusted under 35 U.S.C. 154(b) by 0 days.

(21) Appl. No.: 09/931,640

(22) Filed: Aug. 15, 2001

(65) Prior Publication Data

US 2002/0054912 A1 May 9, 2002

Related U.S. Application Data

(60) Provisional application No. 60/225,525, filed on Aug. 15, 2000, and provisional application No. 60/225,620, filed on Aug. 15, 2000.

(51) Int. Cl.[7] .............................................. A61K 9/14
(52) U.S. Cl. ...................... 424/489; 424/400; 424/490
(58) Field of Search ................................ 424/400, 489, 424/490

(56) References Cited

U.S. PATENT DOCUMENTS

| 5,019,400 A | | 5/1991 | Gombotz et al. ............ 424/497 |
| 5,340,090 A | * | 8/1994 | Orme et al. ................. 266/202 |
| 5,344,676 A | | 9/1994 | Kim et al. .................... 427/468 |
| 5,650,173 A | | 7/1997 | Ramstack et al. ........... 424/489 |
| 5,654,008 A | | 8/1997 | Herbert et al. .............. 424/489 |

(List continued on next page.)

FOREIGN PATENT DOCUMENTS

| CH | 675370 A5 | 9/1990 | ............ B01J/13/02 |
| DE | 27 25 849 A1 | 12/1978 | ............. A61J/3/06 |
| EP | 0 265 924 A2 | 4/1988 | ............. B29B/9/00 |
| WO | WO 97/31691 | 4/1997 | ............ B01B/11/00 |
| WO | WO 99/44735 | 10/1999 | ............ B01J/13/04 |

OTHER PUBLICATIONS

K. Kim and R.J. Turnbull, "Generation of charged drops of insulating liquids by electrostatic spraying," J. Appl. Phys., vol. 47, No. 5, pp. 1964–1969, May 1976.

N. Leelarasamee, S. A. Howard, C. J. Malanga and J. K. H. Ma, A method for the preparation of polylactic acid microcapsules of controlled particle size and drug loading. J. Microencapsul. 5 (1988) 147–157.

N.K. Kim, K. Kim, D.A. Payne, and R.S. Upadhye, "Fabrication of hollow silica aerogel spheres by a droplet generation method and sol–gel processing," J. Vac. Sci., Technol. A., vol. 7, No. 3 pp. 1181–1184 (1989).

K. Kim, K.Y. Jang and R.S. Upadhye, "Hollow silica spheres of controlled size and porosity by sol–gel processing," J. Am. Ceram. Soc., 74:8, pp. 1987–1992, (1991).

P. Sansdrap and A. J. Moes, Influence of manufacturing parameters on the size characteristics and the release profiles of nifedipine from poly(DL–lactide–co–glycolide) microspheres. Int. J. Pharm. 98 (1993) 157–164.

K. Shiga, N. Muramatsu and T. Kondo, Preparation of poly(D,L–lactide) and copoly(lactide–glycolide) microspheres of uniform size. J. Pharm. Pharmacol. 48 (1996) 891–895.

B. G. Amsden and M. Goosen, An examination of the factors affecting the size, distribution, and release characteristics of polymer microbeads made using electrostatics. J. Control. Relase 43 (1997) 183–196.

(List continued on next page.)

Primary Examiner—Michael G. Hartley
Assistant Examiner—Konata M George
(74) Attorney, Agent, or Firm—Sonnenschein Nath & Rosenthal LLP

(57) ABSTRACT

A method of forming particles comprises accelerating a stream comprising a liquid; and vibrating the stream, to form particles. The particle may have a diameter that is smaller than the diameter of the nozzle used to form the stream, allowing for the formation of micro- and nano-sized particle.

59 Claims, 7 Drawing Sheets

U.S. PATENT DOCUMENTS

| | | | |
|---|---|---|---|
| 5,667,808 A | 9/1997 | Johnson et al. | 424/501 |
| 5,674,534 A | 10/1997 | Zale et al. | 424/501 |
| 5,711,968 A | 1/1998 | Tracy et al. | 424/487 |
| 5,716,644 A | 2/1998 | Zale et al. | 424/497 |
| 5,792,477 A | 8/1998 | Rickey et al. | 424/501 |
| 5,817,343 A | 10/1998 | Burke | 424/489 |
| 5,891,478 A | 4/1999 | Johnson et al. | 424/502 |
| 5,912,015 A | 6/1999 | Bernstein et al. | 424/484 |
| 5,916,597 A | 6/1999 | Lee et al. | 424/501 |
| 5,916,598 A | 6/1999 | Rickey et al. | 424/501 |
| 5,922,253 A | 7/1999 | Herbert et al. | 264/5 |
| 5,989,463 A | 11/1999 | Tracy et al. | 264/4.1 |
| 6,051,259 A | 4/2000 | Johnson et al. | 424/502 |
| 6,060,128 A | 5/2000 | Kim et al. | 427/483 |
| 6,110,503 A | 8/2000 | Rickey et al. | 424/501 |
| 6,110,921 A | 8/2000 | Mesens et al. | 514/258 |
| 6,116,516 A | 9/2000 | Ganan-Calvo | 239/8 |
| 6,119,953 A | 9/2000 | Ganan-Calvo et al. | 239/8 |
| 6,153,129 A | 11/2000 | Herbert et al. | 264/5 |
| 6,174,469 B1 | 1/2001 | Ganan-Calvo | 264/12 |
| 6,183,781 B1 | 2/2001 | Burke | 424/486 |
| 6,187,214 B1 | 2/2001 | Ganan-Calvo | 216/92 |
| 6,189,803 B1 | 2/2001 | Ganan-Calvo | 239/5 |
| 6,194,006 B1 | 2/2001 | Lyons et al. | 424/489 |
| 6,196,525 B1 | 3/2001 | Ganan-Calvo | 261/76 |
| 6,197,835 B1 * | 3/2001 | Ganan-Calvo | 516/10 |
| 6,224,794 B1 | 5/2001 | Amsden et al. | 264/4.1 |

OTHER PUBLICATIONS

B. Amsden, The production of uniformly sized polymer microspheres. Pharm. Res. 16 (1999) 1140–1143.

"Fabrication of PLG microspheres with precisely controlled and monodisperse size distributions" J. Controlled Release 73(1):59–74 (May 18, 2001).

Aldrich Technical Bulletin, AL–203, 1997.

Berkland, C., et al., *J. of Cont. Release,* 2001, vol. 73, p. 59–74.

Bittner, B. and Kissel, T., *Microencapsulation,* 1999, vol. 16:3, p. 325–341.

Shiga, K. et al., *J. Pharm. Pharmacol.,* 1996, vol. 48, p. 891–895.

\* cited by examiner

MICROPARTICLES

RELATED APPLICATIONS

The present application claims the benefit of two provisional applications, Provisional application serial No. 60/225,525 filed Aug. 15, 2000, to Kyekyoon Kim and Daniel W. Pack, entitled "PRECISE, CONTROLLED POLYMER FABRICATION FOR BIOMEDICAL APPLICATIONS"; and Provisional application serial No. 60/225,620 filed Aug. 15, 2000, to Kyekyoon Kim, entitled "APPARATUS AND METHOD FOR FABRICATION OF UNIFORM SOLID AND HOLLOW SPHERICAL PARTICLES IN THE MICRON- AND SUBMICRON-RANGE AND SUCH PARTICLES OF CONTROLLED SIZES, ELECTRICAL CHARGES, CHEMICAL COMPOSITIONS AND STOICHIOMETRIES USING FIELD-INJECTION CHARGING AND ELECTROHYDRODYNAMIC SPRAYING"; both of which are hereby incorporated by reference.

BACKGROUND

Rapid advances in biotechnology have led to the discovery of numerous protein and peptide therapeutics, many of which have recently reached the marketplace or are currently under regulatory review by the United States Food and Drug Administration. Unlike traditional small-molecule drugs, however, proteins and peptides generally cannot be administered orally; injection or infusion is most often required. Further, because of their fragility and short in vivo half-lives, encapsulation of proteins in biodegradable polymeric devices, from which the drug can be delivered, locally or systemically, for a prolonged period of time, has been a promising and intensely studied solution to these problems. Biodegradable microspheres comprising a variety of polymers have been the most studied devices due to relatively simple fabrication and facile administration to a variety of locations in vivo through a syringe needle.

Several methodologies for microsphere fabrication have been described, including precipitation, spraying, phase separation, and emulsion techniques. The emulsion and spraying approaches have been commonly used both at the bench and industrial scales. Sphere size and size distribution are reproducible but often poorly controllable. Standard deviations equal to 25–50% of the mean diameter are not uncommon.

Control of sphere size and size distribution has several important implications for controlled-release drug delivery. For example, there typically is an ideal sphere size that provides a desired release rate and route of administration. Spheres that are "too small" exhibit poor encapsulation efficiency, may migrate from the site of injection, and may exhibit undesirably rapid release of their payload. Spheres that are "too large" may not easily pass through a syringe needle. Thus, the typically polydisperse spheres generated by conventional fabrication techniques must be filtered or sieved to isolate particles within the desired size range, and the polymer and drug composing spheres outside that range are wasted.

Uniform microspheres approximately 1–5 $\mu$m in diameter would be ideal for passive targeting of professional antigen-presenting cells (APCs) such as macrophages and dendritic cells. Similarly, microspheres 10–20 $\mu$m in diameter could be used to target the tortuous capillary bed of tumor tissues by chemoembolization. A system capable of precise microsphere fabrication could allow the optimal size for such applications to be identified and provide an efficient route to commercial manufacture and clinical implementation.

A long-sought goal for controlled-release drug delivery technologies is the ability to precisely control the release rate of encapsulated compounds, and microsphere size is a major determinant of release kinetics. Larger spheres generally release encapsulated compounds more slowly and over longer time periods, other properties (polymer molecular weight, initial porosity, drug distribution within the sphere, etc.) being equal. A constant (i.e., zero-order) release rate is often preferred, while variable drug release rates can be beneficial for many important indications. For example, intermittent high doses of antibiotics may alleviate evolution of resistance in bacteria, and discontinuous administration of vaccines often enhances the immune response.

Methods to control drug release rate include (i) choice of polymer chemistry (anhydrides, esters, etc.) and comonomer ratios, (ii) conjugating the drug to the polymer, (iii) varying the microsphere formulation parameters, and thus the physical characteristics of the resulting particles, and (iv) manipulating the sphere size and distribution. The success of the latter studies was limited by the relatively broad microsphere size distributions.

In recent years, there have been several reports of the fabrication of biodegradable polymer microspheres with controlled, uniform size (P. Sansdrap and A. J. Moes, Influence of manufacturing parameters on the size characteristics and the release profiles of nifedipine from poly(-zDL-lactide-co-glycolide) microspheres. Int. J. Pharm. 98 (1993) 157–164; B. G. Amsden and M. Goosen, An examination of the factors affecting the size, distribution, and release characteristics of polymer microbeads made using electrostatics. J. Control. Release 43 (1997) 183–196; K. Shiga, N. Muramatsu and T. Kondo, Preparation of poly(D,L-lactide) and copoly(lactide-glycolide) microspheres of uniform size. J. Pharm. Pharmacol. 48 (1996) 891–895; B. Amsden, The production of uniformly sized polymer microspheres. Pharm. Res. 16 (1999) 1140–1143; and N. Leelarasamee, S. A. Howard, C. J. Malanga and J. K. H. Ma, A method for the preparation of polylactic acid microcapsules of controlled particle size and drug loading. J. Microencapsul. 5 (1988) 147–157). However, none of these methods was successful in generating particles in a size range appropriate for drug delivery (~1–100 $\mu$m) while maintaining narrow size distributions. In addition, these previous methods appear to be difficult to scale-up for commercial applications.

Hollow sphere fabrication techniques are disclosed in N. K. Kim, K. Kim, D. A. Payne, and R. S. Upadhye, "Fabrication of hollow silica aerogel spheres by a droplet generation method and sol-gel processing," *J. Vac. Sci., Technol. A.,* vol. 7, no.3 pp. 1181–1184 (1989) and K. Kim, K. Y. Jang and R. S. Upadhye, "Hollow silica spheres of controlled size and porosity by sol-gel processing," *J. Am. Ceram. Soc.,* 74:8, pp. 1987–1992, (1991).

Electrostatic spraying technique is disclosed in K. Kim and R. J. Turnbull, "Generation of charged drops of insulating liquids by electrostatic spraying," *J. Appl. Phys.,* vol. 47, no. 5, pp. 1964–1969, May 1976, U.S. Pat. No. 5,344,676 to Kim et al., and U.S. Pat. No. 6,060,128 to Kim, et al.

Previously developed techniques designed to fabricate hollow spheres employ a dual-nozzle scheme in which two coaxially mounted nozzles carrying different materials in liquid phase (the material in the inner nozzle could also be a gas) produce a smooth cylindrical jet which, in turn, is broken up into uniform droplets by an acoustic excitation. (See N. K. Kim, et al., "Fabrication of hollow silica aerogel spheres by a droplet generation method and sol-gel processing," infra and K. Kim et al., "Hollow silica spheres of controlled size and porosity by sol-gel processing," infra). The smallest drops that can be made with this method are roughly twice as large as the opening of the outer nozzle. This in turn indicates practical difficulties associated with fabricating uniform solid and hollow spheres of small sizes (less than about 50 µm in diameter) especially spheres in the submicron-size range. The reason is that the smaller the nozzle opening, the greater the chances for it to get plugged up, especially if the pharmaceutical compounds to be encapsulated are suspended as a particulate in the sphere-forming liquid. This problem becomes worse when the materials being used are viscous.

With previous technologies for spraying microdroplets from nozzle-type devices, the minimum sphere size typically obtainable is limited by the size of the nozzle opening. Usually, it is not possible to make drops smaller than the nozzle opening; typically, droplet diameters are 1–4 times the diameter of the nozzle. This presents several difficulties as the desired sphere size decreases. One problem is that fabrication of the nozzles themselves becomes more difficult as size decreases. This is especially true for large-scale fabrication methods in which it is necessary to form droplets through arrays of nozzles (perhaps 1000–2000). A second limitation stems from the pressure needed to pump fluids through small nozzles. The pressure required is given by $$\Delta p = \frac{8\mu LQ}{\pi R^4}$$

where $\Delta p$ is the pressure drop across the nozzle, $\mu$ is the viscosity of the fluid, L is the length of the nozzle "passage", Q is the volumetric flow rate of the fluid passing through the nozzle, and R is the radius of the nozzle opening. Thus, the pressure required scales with $R^{-4}$. If one wishes to make microdroplets of ~5 µm diameter, traditional methods may require a nozzle with a diameter of 5 µm or less. For example, at a flow rate of 1 mL/min and a fluid viscosity of 100 centipoise (100-times more viscous than water), a 5-µm diameter orifice would require a pump head of ~$1.1 \times 10^{10}$ Pa (~110,000 atm). This is clearly an impossibly high pressure. Even water, $\mu$~1 cp, requires a pressure of 1,100 atm to be pumped through a 5-µm diameter nozzle at 1 mL/min. Thus, pumping virtually any liquid through a nozzle of 5-µm diameter would require special equipment, if it could be done at all.

Another problem with traditional methods of forming small spheres is that some compounds to be encapsulated, such as plasmid DNA, may be damaged by shear forces. Damage depends on the product of the shear rate, γ, and the time spent in the shear field, θ. The average value of this product for a fluid flowing through a pipe is given by $(\gamma\theta)_{avg} = 16/3 \cdot (L/D)$ where L is the length of the pipe and D is the pipe diameter. The orifice of a nozzle can be approximated as a pipe. However, entrance effects will tend to increase the shear rate meaning this equation will give a low estimate. Regardless, the value of γθ is approximately inversely proportional to the diameter of the orifice. Thus, decreasing the nozzle diameter from 100 to 5 µm would increase the damage done to any encapsulated compound by a factor of 20.

U.S. Pat. No. 6,116,516 describes stabilized capillary microjets, that produce aerosols. The microjets are formed by forcing a gas around a liquid stream. Under the correct conditions, micron-sized aerosols are produced, where preferably 90% or more have the same diameter plus/minus 3% to 30%.

BRIEF SUMMARY

It is an object of this invention to produce micro- and nano-sized spherical particles by pumping material through a small orifice and then shaking said liquid with an acoustic type-wave.

It is also an object of this invention to produce micro- and nano-sized spherical particles by pumping a material through a small orifice and adding an additional downward force, said downward force comprising either electrohydrodynamic technique or a second liquid stream adjacent and parallel to the liquid at a velocity greater than the first liquid. It is also an object of this invention to produce uniform micro- a nd nano-sized spherical particles by using acoustic type waves with the above process.

It is a further object of this invention to produce hollow micro- a nd nano-sized spherical particles by utilizing an inside and outside liquid that are passed through one or the other of two coaxially mounted nozzles to produce a smooth cylindrical jet of the outside liquid coaxially containing the inside liquid (or gas). This jet can be further broken into uniform droplets by acoustic waves.

It is yet a further object of this invention to provide a novel process for hardening micro- and nano-spheres by utilizing any of the above processes for producing micro- and nano-spheres, wherein the nozzle or orifice utilized is placed beneath the surface of an aqueous bath, to allow hardening of the spheres with a minimum of deformation.

It is still a further object of this invention to produce therapeutic compounds, encapsulated by any of the above techniques useful as biomedical compositions for medical treatment of humans and therapeutic value.

It is yet another object of this invention to produce multi-shelled micro- and nano-spheres of controlled sizes, shell thicknesses and number of shells with different shells comprising different materials useful for biomedical applications for humans and animals including controlled-release drug delivery systems.

It is still a further object of this invention to produce micro- a nd nano-spheres of the types described above, and other types, for biomedical applications including passive or active targeting to desired cells, tissues or regions of the body.

It is a further object of this invention to provide an apparatus and process for producing micro- and nano-spherical particles of precisely controlled sizes and size distributions for biomedical applications, especially controlled-release drug delivery systems.

It is a further object of this invention to produce stable micro- and nano-spheres of a desired size, chemical composition and stoichiometry.

It is a further object of this invention to produce micro- and nano-spheres of controlled sizes for biomedical applications including controlled-release drug delivery systems.

It is yet a further object of this invention to produce hollow micro- and nano-spheres of controlled sizes for biomedical applications including controlled-release drug delivery systems.

These and other objects are provided in this invention which is described in more detail hereafter.

In a first aspect, the present invention is a method of forming particles, comprising accelerating a first stream comprising a first liquid; and vibrating the first stream, to form particles.

In a second aspect, the present invention is a method of forming particles, comprising accelerating a first stream comprising a first liquid. The accelerating comprises applying charge to the first stream. The particles comprise a core and a shell.

In a third aspect, the present invention is particles having an average diameter of 50 to 100 µm. Ninety percent of the particles have a diameter that is within 2% of an average diameter of the particles.

In a fourth aspect, the present invention is particles having an average diameter of 1 to 50 µm. Ninety percent of the particles have a diameter that is within 1 µm of an average diameter of the particles.

In a fifth aspect, the present invention is particles, prepared by the above method.

In a sixth aspect, the present invention is an apparatus for forming particles, comprising (i) a first nozzle, for forming a first stream of a first liquid, (ii) a second nozzle, oriented for forming a second stream of a second liquid in contact with the first stream, and (iii) a vibrator, for forming particles from the first stream.

In a seventh aspect, the present invention is an apparatus for forming particles, comprising (i) a first nozzle, for forming a first stream of a first liquid, (ii) a charge source, for applying charge to the first stream, and (iii) a vibrator, for forming particles from the first stream.

In an eighth aspect, the present invention is an apparatus for forming particles, comprising (i) means for forming a first stream of a first liquid, (ii) means for accelerating the first stream, and (iii) means for vibrating the first stream.

In a ninth aspect, the present invention is an apparatus for forming particles, comprising (i) a first nozzle, for forming a first stream of a first liquid, (ii) a second nozzle surrounding the first nozzle, for forming a second stream of a second liquid surrounding the first stream, (iii) a charge source, for applying charge to at least one of the first and second streams.

In a tenth aspect, the present invention is a method of making particles, comprising forming particles with the above apparatuses.

BRIEF DESCRIPTION OF THE DRAWINGS

FIG. 4D demonstrates application of an increasing potential to the nozzle.

FIG. 6 also demonstrates the rhodamine B release from spheres over the course of 7–10 days of incubation in PBS and 37° C. The release rate was faster when spheres contained more drug as would be expected.

DETAILED DESCRIPTION

Figure 1:
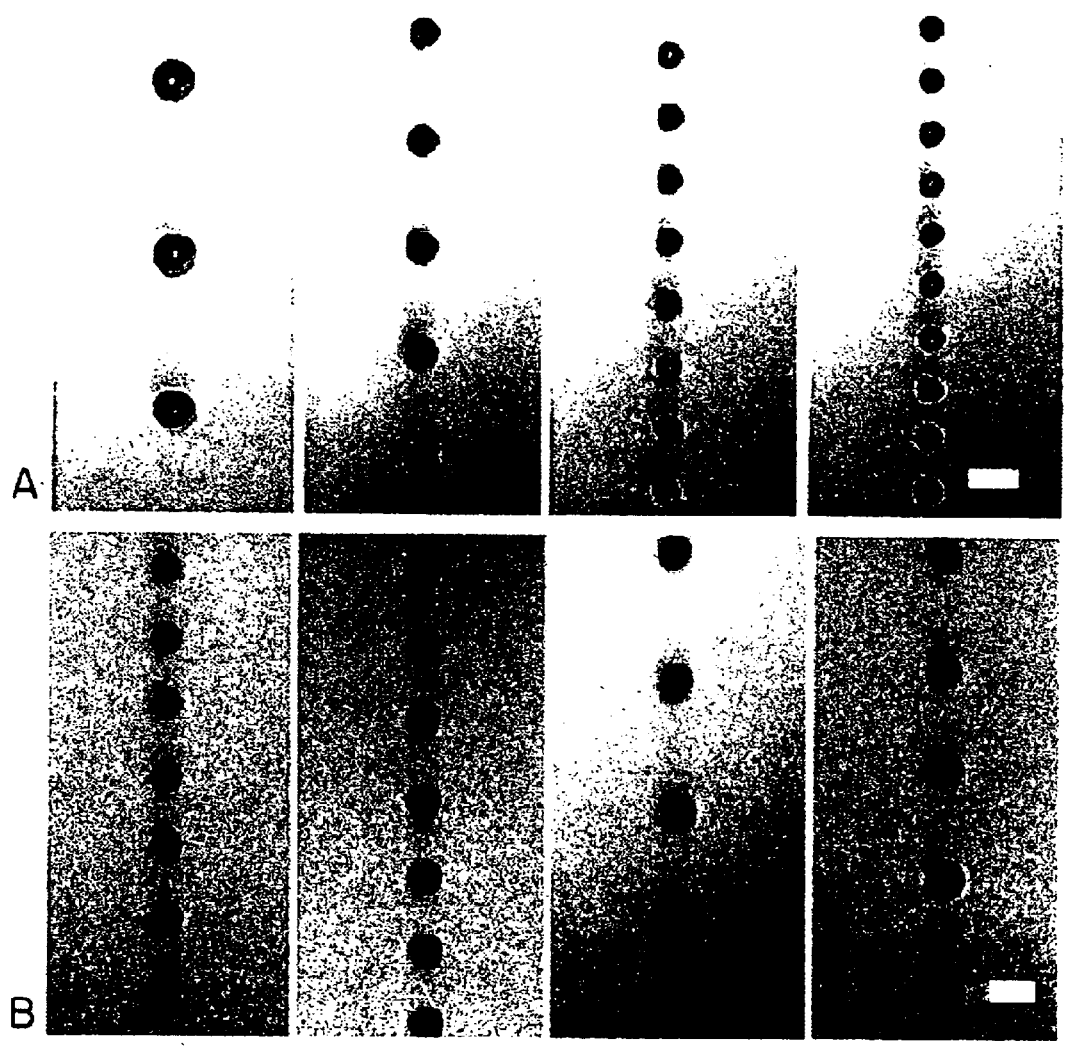
FIG. 1 displays free-falling spheres illuminated with a strobe lamp and the images were captured on videotape using a 10×microscope objective and a CCD camera.

The present invention relates to a process wherein micro- a nd nano-sized particles, preferably spherical, are produced by pumping material through a small orifice and then shaking said liquid with an acoustic type-wave, where the velocity of the fluid is increased beyond the velocity produced by pressure behind the liquid. The nozzle diameter may be larger than the particles produced. For example, 5-µm droplets can be prepared from a much larger nozzle, for example a nozzle of 100 µm diameter. The particles are formed within a surrounding liquid, helping to prevent deformation.

The pressures needed to form very small particles are greatly reduced with the present invention. For example, a 100-cp solution pumped through a 100-µm diameter nozzle at 1 mL/min would require a pump pressure of only ~68,000 Pa (~0.67 atm), or a solution as viscous as glycerin ($\mu$~500 cp) can be pumped through a 100-µm diameter nozzle at 5 mL/min with a pump head of 15 atm. These pressures are easily obtained with commercial high-pressure pumps such as those commonly supplied with high-pressure liquid chromatography systems. Furthermore, the shear forces are greatly reduced for a given particles size, and the difficulties encountered with very small diameter nozzles are also eliminated. Aspects of the invention are described in "Fabrication of PLG microspheres with precisely controlled and monodisperse size distributions" J. Controlled Release 73(1):59–74 (May 18, 2001), hereby incorporated by reference.

The present invention also relates to a process wherein micro- and nano-sized spherical particles are produced by pumping a material through a small orifice and adding an additional downward force, said downward force comprising either electrohydrodynamic technique or a second liquid stream adjacent and parallel to the liquid at a velocity greater than the first liquid. Acoustic type waves can also be utilized with the above process. As used herein, the term "particle" includes both liquid particle (droplets) and solid particles.

The present invention further relates to a process for producing hollow micro- a nd nano-sized spherical particles wherein an inside and outside liquid are passed through one or the other of two coaxially mounted nozzles to produce a smooth cylindrical jet of the outside liquid coaxially containing the inside liquid (or gas). This jet can be further broken into uniform droplets by acoustic waves.

The present invention further provides a novel process for hardening micro- a nd nano-spheres wherein the nozzle or orifice utilized to produce said spheres is placed beneath the surface of an aqueous bath, to allow hardening of the spheres with a minimum of deformation.

This invention still further provides therapeutic compounds, encapsulated by any of the above techniques useful as biomedical compositions.

One embodiment of the present invention employs "Electrohydrodynamic Spraying" and "Dual-nozzle Method" independently or in combination to produce very small uniform solid, hollow or multi-shell spheres. The incorporation of electrohydrodynamic spraying to enable fabrication of hollow and multi-shell micro- a nd nano-spheres is new. This technique is novel and very useful in that it is particularly suited to fabricating micrometer- and nanometer-size hollow and multi-shell spheres which would be essentially impossible to create with any other existing techniques. Further, encapsulation of therapeutic compounds in very uniform spheres, and especially in hollow and multi-shelled spheres, is novel and very useful for controlled-release and targeted drug delivery with precisely controlled release rates which can not be obtained using spheres fabricated by other existing techniques.

The apparatus and method of this invention allow for the encapsulation of a first material in a spherical shell of a second material which will be particularly useful for various biomedical applications.

The apparatus and method of this invention also allows for the production of solid spheres of only the second material by blocking the supply of the first material though the inner nozzle.

Another unique and novel aspect of this invention is that this approach can be utilized to choose the electrical polarity (neutral, positive or negative) of the resulting micro- a nd nano-spheres.

This concept can be extended to fabricate multi-shell spheres comprising more than two kinds of materials. The fact that the invention allows one to produce very small multi-shell spheres smaller than 50 or 100 $\mu$m in diameter makes it particularly useful in applications involving drug delivery systems (DDS). Numerous applications other than the DDS should also be possible.

The instant invention also provides for solid or hollow uniform micro- a nd nano-spheres of controlled sizes, shell thicknesses, electrical charges, chemical compositions and stoichiometries. Such spheres have many unique applications in the biomedical field.

The instant invention relates to a process for making micro- and nano-sized spherical particles comprising pumping a material through a small orifice and then shaking said liquid with an acoustic type-wave to produce micro- and nano-sized spherical particles.

The instant invention further relates to a process for making micro- and nano-sized spherical particles comprising pumping a material through a small orifice and adding an additional downward force to said liquid to pull the liquid through the orifice. The additional downward force can be an electrohydrodynamic technique or a second liquid stream, adjacent and parallel to the liquid, at a velocity greater than the sphere forming liquid. These processes can be further modified by the addition of acoustic type waves.

The instant invention further relates to a process for making hollow micro- and nano-sized spherical particles comprising an inside and outside liquid, wherein the inside and outside liquid are passed through one or the other of two coaxially mounted nozzles, wherein a smooth cylindrical jet is generated of the outside liquid coaxially containing the inside liquid (or gas) inside of said outside liquid. This jet can be broken into uniform droplets by acoustic waves. The size and ratio between the radius and thickness of the hollow spheres is controlled by varying the relative flow rates of the outer and inner liquids, the relative sizes of the nozzles, the relative positioning of the nozzles, and the amplitude and frequency of the acoustic excitation.

This method further facilitates fabrication of hollow spheres of large ratios between the radius and thickness of the hollow spheres since the surface tension of the bath liquid helps retain the spherical shape and integrity of the hollow spheres.

The instant invention further relates to a process for hardening micro- and nano-spheres by utilizing any of the above processes for producing micro- and nano-spheres, wherein the nozzle or orifice utilized is placed beneath the surface of an aqueous bath, to allow hardening of the spheres with a minimum of deformation. Any of the above nozzle types work with this embodiment of the invention.

This invention further relates to therapeutic compounds, encapsulated by any of the above techniques given to humans for medical treatment.

The instant invention relates to a process for the production of micro and nano-spheres comprising the use of the dual nozzle system and the electrohydrodynamic concept to produce micro and nano-sized spherical particles.

This invention further relates to the use of a very sharp hypodermic type needle in the inner nozzle of the dual nozzle system, to produce solid, hollow and multi-shell micro- and nano-sized particles useful as semi-conductors and biomedical applications.

This invention further relates to novel biomedical compositions comprising uniform solid, hollow and multi-shell micro- and nano-sized particles, hollow and filled.

In this application the terms spheres, beads and particles are used interchangeably to describe the micro- and nano-spheres of the instant invention. Also, the term "hollow" is used to indicate that the core is empty or contains a gas. The term "multi-shell" includes particles wherein the core is a liquid (aqueous, oil, etc . . . ) or a solid such as another polymer. Although the terms "hollow" and "multi-shell" are utilized differently in the instant application, these terms should be read as including the other.

A need exists in the biomedical industry for the production of micro- and nano-sized spheres. The ability to form spheres with precisely controlled sizes, size distributions and morphologies (e.g. hollow, multi-shelled, solid, porous, etc.) has several very important applications, especially in the field of biotechnology. This methodology will allow and/or significantly improve upon many drug delivery technologies.

One embodiment of this invention relates to an apparatus and process for producing solid, hollow and multi-shell, micro- and nano-particles of precisely controlled sizes, size distributions and morphologies for biomedical applications, especially controlled-release drug delivery systems. This invention also relates to novel micro- and nano-spheres, comprising a first material. This invention further relates to novel hollow micro- and nano-spheres of a first material encapsulating a second material.

Another embodiment of this invention relates to an apparatus and process for producing micro- and nano-particles of precisely controlled sizes, size distributions and morphologies for biomedical applications, especially controlled-release drug delivery systems.

An embodiment of this invention allows for particle or sphere formation by pumping a liquid material (e.g., polymer dissolved in organic solvent, polymer melts, etc.) through a small orifice wherein the small orifice can be from several millimeters to about 1 micrometer in diameter. The orifice can even be as small as 500 nm in diameter. The stream of liquid exiting the orifice is broken into droplets by vibrating or shaking the device at a controlled frequency and amplitude.

The vibration or shaking can be achieved by, for example, a piezoelectric transducer driven by a wave generator. It is believed that the mechanical excitation launches a wave of acoustic energy along the liquid jet generating periodic instabilities that, in turn, break the stream into a train of uniform droplets.

Droplet size is determined by the orifice diameter, the solution flow rate, the vibration frequency and amplitude. Thus, by varying these four parameters droplet size can be controlled. Furthermore, given an apparatus with a fixed orifice, droplet size can be varied within a range from a minimum size slightly larger than the orifice opening to a maximum at least 10-times the orifice opening.

This approach represents an improvement over conventional ultrasonic nozzles as the acoustic wave intensity is lower and one can tightly control the match between the frequency and solution flow rate.

In yet another embodiment of this invention, sphere size can be further controlled by employing an additional downward force that will 'pull' the liquid jet through the orifice, reducing the jet size below the diameter of the orifice. One example is an electrohydrodynamic technique in which electrical forces act to reduce the diameter of the liquid jet and the resulting droplets. The electrohydrodynamic technique is activated through injection of charge of desired polarity into the liquid by applying a high voltage either to the nozzle or directly into the liquid, for example, with a battery, or with a transformer and a rectifier to convert household current. Outwardly directed electrical tension forces result at the charged liquid meniscus of the nozzle opening, enabling a smaller drop to fall from the nozzle (the "drip mode"). Not to be bound by theory, the reason for this reduction in drop size is believed to be that there are two forces present, gravitational and electrical, that are working together to pull the liquid off of the nozzle, while surface tension forces hold the liquid at the nozzle. As the amount of charge injected increases, the electrical tension forces accordingly increase, eventually dominating the gravitational and surface-tension forces and reducing the drop size. Further increase in charge injection beyond a certain threshold value results in very powerful electrical tension forces that literally pull the liquid out of the nozzle to form a thin charged liquid jet, which in turn breaks up into fairly uniform droplets (known as the "jet mode"). Jet mode changes from single-jet to multi-jet mode as charge injection is further increased.

Another example of an additional downward force employed is a separate liquid stream (typically immiscible) through the orifice, adjacent and parallel to the sphere-forming liquid, at a velocity greater than the sphere-forming liquid. The sphere-forming liquid is pulled along by the drag forces at the liquid/liquid interface. The sphere-forming jet is reduced in diameter by a factor that is proportional to the difference in linear velocities of the two streams.

The technique of this invention can be further modified to generate "hollow" or multi-shell particles comprised of two or more concentric spheres of different materials. Spheres consisting of a polymer shell surrounding a drug-containing aqueous phase, for example, can be generated. Such spheres can be formed using the dual nozzle method which consists of utilizing two coaxially mounted nozzles. By passing the two liquids through one or the other of the nozzles, a smooth cylindrical jet of one liquid coaxially containing another liquid (or gas) inside of it can be generated. The jet can then be broken into uniform droplets using acoustic waves, as described above, resulting in the "hollow" or multi-shell spheres. The size and the ratio between the radius and thickness of the spheres can be controlled by varying the relative flow rates of the outer and inner fluids, the relative sizes of the nozzles, the relative positioning of the nozzles and the amplitude and frequency of the acoustic excitation.

Another embodiment of this invention allows for the novel hardening of micro- and nano-spheres while allowing the spheres to retain their uniformity. Droplets falling from the apparatus can be hardened to form micro-spheres by any of several standard methods depending on the type of material comprising the spheres. An important consideration is maintaining the uniform size or desired size distribution during sphere collection, hardening (phase inversion) and drying. If the droplets exiting the nozzle are allowed to fall through the air and then enter a liquid bath (often aqueous or liquid nitrogen) where the organic solvent is to be extracted, for example, the impact of the spheres with the liquid surface may deform, or even completely disrupt the sphere morphology. Another embodiment of the instant invention overcomes this inherent problem in the art, wherein the embodiment is a method in which the orifice is placed beneath the surface of an aqueous bath, thus avoiding the impact with the surface, The spheres are subsequently agitated to allow the organic solvent to be efficiently extracted. But the agitation must be gentle; normal stirring speeds cause too much shear force and break the particles, ruining the size distribution. This is believed to be novel since other spraying methods do not utilize a nozzle placed below a liquid/air interface.

In one embodiment the instant invention utilizes electrohydrodynamic spraying in combination with a dual nozzle method to produce very small uniform spheres which are hollow. Micro- and nano-spheres of desired size, chemical composition and stoichiometry can be produced in the most stable manner through this novel process, named flow-limited field injection electrostatic spraying (FFESS). This embodiment combines the basic ideas of hollow sphere fabrication technique and the electrostatic spraying technique. Hollow sphere fabrication technique is disclosed in N. K. Kim, K. Kim, D. A. Payne, and R. S. Upadhye, "Fabrication of hollow silica aerogel spheres by a droplet generation method and sol-gel processing," *J. Vac. Sci., Technol. A.*, vol. 7, no. 3 pp. 1181–1184 (1989) and K. Kim, K. Y. Jang and R. S. Upadhye, "Hollow silica spheres of controlled size and porosity by sol-gel processing," *J. Am. Ceram. Soc.*, 74:8, pp.1987–1992, (1991). Electrostatic spraying technique is disclosed in K. Kim and R. J. Turnbull, "Generation of charged drops of insulating liquids by electrostatic spraying," *J. Appl. Phys.*, vol. 47, no. 5, pp. 1964–1969, May 1976, U.S. Pat. No. 5,344,676 to Kim et al., and U.S. Pat. No. 6,060,128 to Kim, et al. In this embodiment, the present invention overcomes the above difficulties by incorporating the concept of electrohydrodynamic spraying. Unlike the usual hollow spheres fabrication techniques in which only mechanical forces are utilized to breakup a smooth liquid jet into uniform hollow droplets, this embodiment of the present invention creates charging of the working liquid and utilizes the resulting electrical tension forces to reduce the size of the liquid jet well below the size of the nozzle opening. This, in turn, reduces the size of the droplets that result from breakup of the liquid jet. In this way one can fabricate uniform multi-shell spheres containing different materials that are very small: smaller than 50 $\mu$m in diameter. This particular capability of the present invention should enable one to encapsulate nano-meter-size particles inside a spherical shell comprising a chosen material which coincides with the requirements of many sought after biomedical applications involving controlled drug release or drug delivery systems. The ability to control the thickness of and the material comprising the outer spherical shell should also facilitate formulation of a variety of scenarios for the control of drug release dynamics. It must be emphasized that the same method applies to coaxial nozzles containing more than two nozzles allowing for fabrication of small multi-shell spherical particles with two or more layers of different materials.

The particles of the present invention may have a very narrow size distribution. Preferably, at least 90% of the particles have a diameter that is within 2%, more preferably within 1%, of the average particle diameter. Alternatively, preferably at least 95% of the particles have a diameter that is within 10%, more preferably within 5%, even more preferably within 2%, and most preferably within 1%, of the average particle diameter. Alternatively, preferably, at least 95% of the particles have a diameter that is within 10%, more preferably within 5%, even more preferably within 2%, and most preferably within 1%, of the average particle diameter. Alternatively, preferably, at least 98% of the particles have a diameter that is within 10%, more preferably within 5%, even more preferably within 2%, and most preferably within 1%, of the average particle diameter. Alternatively, preferably, at least 99% of the particles have a diameter that is within 10%, more preferably within 5%, even more preferably within 2%, and most preferably within 1%, of the average particle diameter. As used herein, the term "diameter" and "average diameter", in the context of particles, means number average diameter.

Another way to describe a narrow size distribution, preferably with particles have an average diameter of at most 50 $\mu$m, more preferably 1 $\mu$m to 50 $\mu$m, most preferably 1 $\mu$m to 30 $\mu$m, is by the percent that have a diameter that is within a specific length of the average diameter. Preferably, 90% of the particles have a diameter that is within 1 $\mu$m of the average diameter of the particles, more preferably within 0.5 $\mu$m of the average diameter of the particles, most preferably with 0.1 $\mu$m of the average diameter of the particles. Alternatively, preferably 95% of the particles have a diameter that is within 1 $\mu$m of the average diameter of the particles, more preferably within 0.5 $\mu$m of the average diameter of the particles, most preferably with 0.1 $\mu$m of the average diameter of the particles.

This invention relates to an apparatus and process for producing micro- and nano-particles of precisely controlled sizes and size distributions for biomedical applications, especially controlled-release drug delivery systems. This invention also relates to novel micro- and nano-spheres, comprising a first material. This invention further relates to novel hollow micro- and nano-spheres of a first material encapsulating a second material.

This invention relates to an apparatus and process for producing micro- and nano-particles of precisely controlled sizes and size distributions for biomedical applications, especially controlled-release drug delivery systems.

This invention further relates to the use of a very sharp hypodermic type needle in the inner nozzle of the dual nozzle system, to produce solid, hollow and multi-shell micro- and nano-sized particles useful as semi-conductors and biomedical applications.

Illustratively, particle or sphere formation is accomplished by pumping a liquid material (e.g., polymer dissolved in organic solvent, polymer melts, etc.) through a small orifice (several millimeters to 10 micrometers in diameter). The stream of liquid exiting the orifice is broken into droplets by vibrating or shaking the device at a controlled frequency and amplitude.

The vibration or shaking can be achieved by, for example, a piezoelectric transducer driven by a wave generator. It is believed that the mechanical excitation launches a wave of acoustic energy along the liquid jet generating periodic instabilities that, in turn, break the stream into a train of droplets.

Yet another embodiment of this invention relates to therapeutic compounds. Therapeutic compounds (e.g. peptides, proteins, nucleic acids, polysaccharides, lipids, steroids and organic and inorganic pharmaceutical compounds and the like) can be encapsulated in the spheres by a variety of techniques. Compounds that are soluble in the liquid phase can simply be dissolved. Non-soluble materials can be suspended in the liquid in the form of small particles. Alternatively, non-soluble materials can be dissolved in an immiscible phase and emulsified with the sphere-forming liquid prior to droplet formation. For example, a protein can be dissolved in an aqueous buffer solution while a polymer (the sphere-forming material) can be dissolved in an organic solvent such as methylene chloride or ethyl acetate. The aqueous and organic solutions can be mixed and homogenized to form a water-in-oil emulsion that subsequently becomes the droplet-forming liquid.

An embodiment of this invention utilizes the biodegradable polymer poly(lactic-co-glycolic acid)(PLGA). PLGA is a well-studied polymer for drug delivery and is FDA-approved for a number of in vivo applications. The techniques can, however, be generalized to other materials including poly(orthoesters), poly(anhydrides), poly (phosphoesters), poly(phosphazenes) and others.

Nonlimiting examples of orifices useful for the practice of this invention consist of tapered nozzles, capillary tubes, simple holes in a flat plate, or even an array of multiple orifices of any of these types.

Nonlimiting examples of materials useful for particle formation include polyesters (such as poly(lactic acid), poly(glycolic acid) and poly(lactic-co-glycolic acid)), poly (lactic acid-co-lysine), poly(lactic acid-graft-lysine), polyanhydrides (such as poly(fatty acid dimer), poly(fumaric acid), poly(sebacic acid), poly(carboxyphenoxy propane), poly(carboxyphenoxy hexane), copolymers of these monomers and the like), poly(anhydride-co-imides), poly (amides), poly(ortho esters), poly(iminocarbonates), poly (urethanes), poly(organophasphazenes), poly(phosphates), poly(ethylene vinyl acetate) and other acyl substituted cellulose acetates and derivatives thereof, poly(caprolactone), poly(carbonates), poly(amino acids), poly(acrylates), polyacetals, poly(cyanoacrylates), poly(styrenes), poly (vinyl chloride), poly(vinyl fluoride), poly(vinyl imidazole), chlorosulfonated polyolefins, polyethylene oxide and copolymers and blends thereof.

For applications outside of drug delivery, spheres can be made of virtually any material from polymers (e.g., polystyrene) to metals to inorganics (silica) to cryogenics (frozen hydrogen) so long as the starting precursors are in a liquid phase or solution.

Spheres which can be generated by the instant invention range from about one nanometer to about one millimeter. For drug delivery applications, sizes from about 10 nm to about 100 microns are possible. The term sphere or spheres, as used throughout the application, is not limited to particles having an aspect ratio of 1, but rather includes particles which deviate significantly from perfect spheres. Preferably the particles have an aspect ratio of 1 to 10, more preferably 1 to 2.

The term nano- defines a size in the range of from about 1 to about 1000 nanometers. The term micro-defines a size in the range of from about 1 to about 1000 microns.

The outer shell thickness of a two component bead could be from about 99% of the bead radius to about 1% of the bead radius depending on the application. However, a minimum achievable thickness of the outer shell will depend on the total size of the hollow bead and the properties of the material comprising it. The absolute minimum thickness achievable should be greater than that of a few molecular layers.

The spheres of this invention have many possible biomedical uses.

Passive targeting of phagocytosis. Cells of the immune system, especially macrophages and dendrocytes, are targets for immunization. These "professional" antigen-presenting cells (APCs) can elicit a desired T-cell response to vaccine components. APCs are typically capable of phagocytosis of particles in the range of 1 to 10 $\mu$m; most other types of cells in the body cannot internalize such large particles. By generating in this size range particles containing vaccine components, one can passively target delivery of the vaccine to APCs. Current technologies allow formation of particles of this size, but only with significantly broad size distributions. Our methodology allows generation of vaccine-encapsulating microspheres in which essentially 100% of the spheres are of the desired size. APC targeting can be optimized with no waste of expensive vaccine components in spheres that are too large or too small.

Capillary embolization. Blood vessel size varies throughout the body with the smallest vessels being the capillaries. Tumor tissues typically exhibit particularly tortuous capillary beds that feed the rapidly growing cancer cells. One approach to targeting tumor tissues is to deliver a therapeutic encapsulated in microspheres of a size such that they can become lodged in narrow capillaries. The microspheres are then injected into an artery feeding the tumor. Spheres which are too large will become lodged in larger vessels and the therapeutic may be blocked from reaching all of the tumor. Spheres which are too small will pass through the tumor and could deliver the therapeutic to other healthy tissue; a serious problem since many anti-cancer agents are, of course, cytotoxic. Our ability to generate spheres of a precise size will allow us to maximize the number of spheres lodged in the smallest capillaries and therefore, the amount of therapeutic delivered to the desired location.

Targeting by nano-spheres. Biodegradable polymer spheres less than 1 $\mu$m in diameter (nano-particles or nanospheres) have several specific applications in drug delivery. For example, particles less than 150 nm in diameter can be targeted for receptor-mediated endocytosis by many different types of cells. Nanoparticles are also useful for oral administration wherein the particles can traverse the intestinal epithelium and be taken up by the M-cells and Peyer's patches. Particles that are too large are poorly taken up, particles that are too small contain little therapeutic. Most current methods for biodegradable-polymer nanoparticle formation, of which there are many, result in wide variations in particle size. For example, phase inversion nanoencapsulation, in which polymer and drug are dissolved in a solvent (e.g., methylene chloride) and subsequently poured into a non-solvent phase (e.g., petroleum ether), results in particles of from 100 to 5000 nm. Our ability to control particle size with a maximum variation of a few percent around the average size will allow optimal nanoparticle targeting.

Control of drug release rate from solid microspheres. Many controlled-release drug delivery systems consist of microspheres formed from biodegradable polymers. Therapeutic compounds encapsulated in the microspheres are released as the polymer erodes, most often by hydrolysis, in the aqueous environment within the body. The drug release rate depends on several factors including polymer composition, polymer molecular weight, microsphere porosity, etc. A critical parameter, however, is sphere size. In general, smaller spheres with larger surface area/volume erode and release the therapeutic more quickly than larger spheres.

The ability to precisely control sphere size distribution gives us unprecedented control over drug release rates. By varying liquid flow rate, vibration frequency and amplitude, sphere size can be controlled. Furthermore, by continuously and smoothly varying these three parameters, pre-defined size distributions can be generated. Since drug release rate depends on sphere size distribution, an appropriate size distribution that will provide a desired release rate profile (e.g., zero-order release, pulsatile release, etc.) can then be determined.

Fabrication of composite core/shell microparticles. With the multi-nozzle methodology, composite particles of two or more different materials can be fabricated. Core/shell microparticles for drug delivery have been produced previously, but only with immiscible core and shell phases. In addition, control of sphere size and shell thickness was poor. Fine control of shell thickness and sphere diameter are possible. The two phases could comprise: a gas core within a polymer shell; a drug-containing aqueous core within a polymer shell (the shell could also encapsulate a second or the same compound); a polymer core encapsulating a drug compound within a polymer shell (of the same or different material) encapsulating a second or the same compound. Such particles could produce novel and useful drug-release rate profiles.

Control of drug release rate from microshells. Encapsulation of water-soluble compounds in hydrophobic polymer microspheres typically requires a double-emulsion method in which a drug/aqueous phase is emulsified with a polymer/oil phase. The physical forces necessary for forming the water-in-oil emulsion and contact of the drug with the aqueous/oil interface can be damaging to drug compounds including therapeutic proteins and nucleic acids. Encapsulation in microshells can alleviate this problem as no physical forces are employed and the aqueous/oil interface is greatly reduced in area.

More importantly, microshells present an unprecedented opportunity for controlling drug release rate. Our methodology allows precise control of both the diameter of the sphere and the thickness of the polymer shell. Drug release from biodegradable-polymer microshells, especially those composed of surface-eroding polymers (e.g., polyanhydrides), would be expected to occur in one "burst" once erosion has reduced the shell integrity to some critical minimum. By continuously varying in a particle population the shell thicknesses and the number of microshells of any given shell thickness, virtually any desired drug release rate profile can be generated.

Fabrication of nanoshells. Combination of the electrohydrodynamic and dual-nozzle methodologies will allow fabrication of polymer nanoshells. As above, virtually any compound can be encapsulated in the interior phase of the particle. If DNA (or other nucleic acids) are encapsulated, "artificial virus" particles that may be particularly useful for gene delivery can be produced.

Pharmaceutical compounds which can be encapsulated/released by the instant invention include but are not limited to nucleic acids, proteins and peptides, hormones and steroids, chemotherapeutics, NSAIDs, vaccine components, analgesics, antibiotics, anti-depressants, and the like.

Nucleic acids useful for the practice of this invention include but are not limited to DNA, RNA, peptide-nucleic acids, oligonucleotides, modified to improve stability (e.g., phosphorothioates, aminophosphonates or methylphosphonates).

Proteins and peptides useful for the practice of this invention include but are not limited to human growth hormone, bovine growth hormone, erythropoietin, thrombopoietin, tissue plasminogen activator and derivatives, insulin, monoclonal antibodies (e.g., anti-human epidermal growth factor receptor2 (Herceptin), anti-CD20 (Rituximab), anti-CD 18, anti-vascular endothelial growth factor, anti-IgE, anti-CD 11a) and their derivatives, single-chain antibody fragments, human deoxyribonuclease I (domase alfa, Pulmozyme), type-1 interferon, granulocyte colony-stimulating factor, leutenizing hormone releasing hormone inhibitor peptides, leuprolide acetate, endostatin, angiostatin, porcine factor VIII clotting factor, interferon alfacon-1, pancrelipase (pancreatic enzymes) and the like.

Hormones and steroids (corticosteroids) useful for the practice of this invention include but are not limited to norethindrone acetate, ethinyl estradiol, progesterone, estrogen, testosterone, prednisone and the like.

Chemotherapeutics useful for the practice of this invention include but are not limited to taxol (Paclitaxel), vinblastine, cisplatin, carboplatin, tamoxifen and the like.

NSAIDs useful for the practice of this invention include but are not limited to piroxicam and the like.

Vaccine components useful for the practice of this invention include but are not limited to Hepatitis B, polio, measles, mumps, rubella, HIV, hepatitis A (e.g., Havrix) and the like.

Analgesics useful for the practice of this invention include but are not limited to aspirin, acetaminophen, ibuprofen, naproxen sodium and the like.

Antibiotics useful for the practice of this invention include but are not limited to amoxicillin, penicillin, sulfa drugs, erythromycin, streptomycin, tetracycline, chlarithromycin, ciproflozacin, terconazole, azithromycin and the like.

Anti-depressants useful for the practice of this invention include but are not limited to Zoloft, fluoxetine (Prozac), paroxetine (Paxil), citalopram, venlafaxine, fluvoxamine maleate, imipramine hydrochloride, lithium, nefazodone and the like.

Other biopharmaceutical compounds useful for the practice of the instant invention include but are not limited to sildenafil (Viagra), acyclovir, gancyclovir, fexofenidine, celecoxib (Celebrex), rofecoxib (Vioxx), androstenedione, chloroquine, diphenhydramine HCl, buspirone, doxazocin mesylate, loratadine, clorniphine, zinc gluconate, zinc acetate, hydrocortisone, warfarin, indinavir sulfate, lidocaine, novacaine, estradiol, norethindrone acetate, Medroxyprogesterone, dexfenfluramine, Dextroamphetamine, Doxycycline, thalidomide, fluticasone, fludarabine phosphate, etanercept, metformin hydrochloride, hyaluronate, tetrazocin hydrochloride, loperamide, ibogaine, clonazepam, ketamine, lamivudine (3TC), isotretinoin, nicotine, mefloquine, levofloxacin, atorvastatin (Lipitor), miconazole nitrate (Monistat), ritonavir, famotidine, simvastatin (Zocor), sibutramine HCl monohydrate, ofloxacin, lansoprozole, raloxifene (Evista), zanamivir (Relenza), oseltamivir phosphate, 4-phenylbutyric acid sodium salt, chlorpromazine, nevirapine, zidovudine, cetirizine hydrochloride (Zyrtec) and the like.

Materials which can further be utilized for the practice of this invention can be found in *Physician's Desk Reference* 2000, 54th Edition, ISBN: 1563633302, *AHFS 99 Drug Information*, Amer. Soc. of Health System, ISBN: 1879907917 and U.S. Pat. No. 5,019,400 all incorporated herein by reference in their entirety.

The spheres of the instant invention can have other materials incorporated therein. Materials which can be incorporated into the spheres of the instant invention are selected from the group consisting of salts, metals, sugars, surface active agents, acids, bases, stabilizers and release enhancing agents.

The spheres of this invention can comprise materials incorporated (such as polymers, biopharmaceutical compounds and other ingredients) into the outer shell, into the core, in each shell individually or at various levels of the concentric shells.

An embodiment of this invention comprises a heterogenous mixture of the selected polymer(s) and pharmaceutical compound(s).

One aspect of this invention is an apparatus that will allow practicing of the present invention. The apparatus comprises coaxial multi-nozzle systems connected to appropriate instruments for the control of flow rates of the feed materials, injection charge, and temperature, and for visual characterization of the resulting hollow or multi-layered drops, all of which are in turn controlled by a computer. This apparatus can be controlled by a computer which optimizes processing conditions most suitable for fabricating certain spheres of particular interest and would allow the instruments to produce the multi-shell spheres desired. Such a system can be developed as a complete experimental apparatus for fabricating multi-shell spheres of controlled size, shell thicknesses, chemical composition and stoichiometry. Or such a system may be operated at a central facility to produce spheres that can meet the desired requirements of certain outside users.

Figure 7:
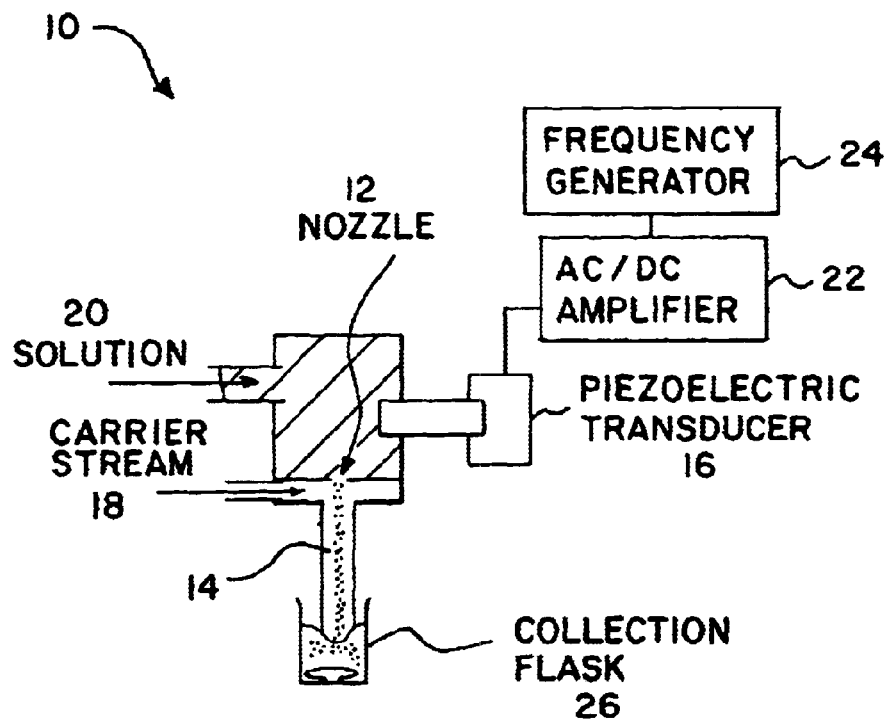
FIG. 7 illustrates an embodiment of an apparatus of the present invention.

An embodiment of an apparatus of the present invention is illustrated in FIG. 7. The apparatus 10 includes a nozzle 12 through which the solution 20 passes, forming a jet 14. A carrier stream 18 of a non-solvent liquid flows around the jet, increasing the velocity of the jet. Vibrations are induced to breakup the jet into particles, in this case using a piezo-electric transducer 16 driven by a frequency generator 24 through an amplifier 22. The particles may be collected in a collection flask 26.

Figure 8:
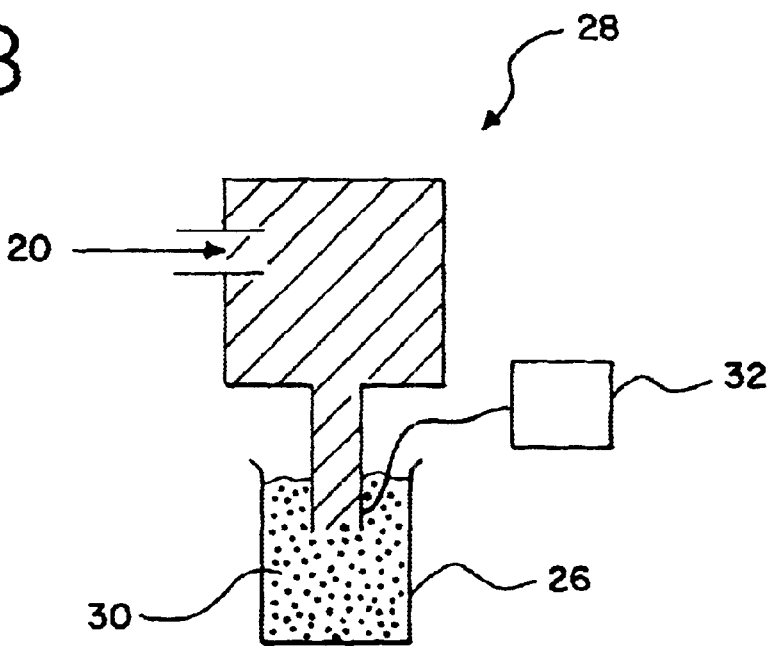
FIG. 8 illustrates another embodiment of an apparatus of the present invention.

Another embodiment of an apparatus of the present invention is illustrated in FIG. 8. The apparatus 28 includes a nozzle 12 through which the solution 20 passes (the jet is not illustrated). The nozzle is within a carrier liquid 30 held within a collection flask 26. A charge source 32 is attached to the nozzle to charge the exiting jet, increasing its velocity. Alternatively, a sharp needle may be attached to the charge source, and inserted into the liquid, to charge the exiting jet; in the case of multiple nozzles (and multiple liquids), the needle may be placed in the most responsive liquid. A ground plate may be included at the collection site. Preferably, vibrations are also induced in the jet, to control the breakup of the jet into particles.

EXAMPLES

The examples herein are illustrations of various embodiments of this invention and are not intended to limit it in any way.

Example 1

Fabrication of Uniform Solid PLGA Microspheres

PLGA was dissolved in ethyl acetate (50 mg/ml) and the solution was pumped through a 60-$\mu$m orifice at varying flow rates from 2–3 mil/min. Simultaneously, the acoustic excitation frequency was varied from 14 to 70 kHz. The free-falling spheres were illuminated with a strobe lamp and the images were captured on videotape using a 10×microscope objective and a CCD camera. As shown in FIG. 1, spheres that are homogenous in size from 65 to 120 $\mu$m have been fabricated (note that the minimum sphere size is only slightly larger than the orifice diameter). The sphere size increased with increasing polymer solution flow rate and decreasing ultrasound frequency.

Figure 2:
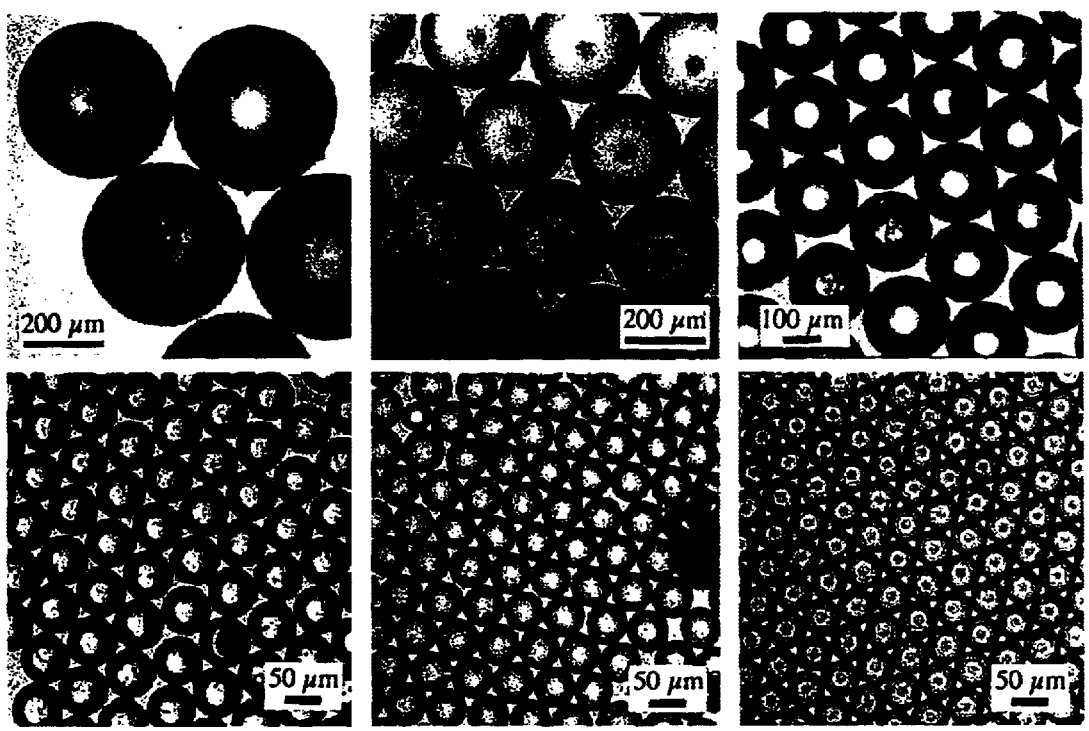
FIG. 2 illustrates the homogeneity of sphere diameters within a single preparation from 15–500 µm.

Uniform spheres have been formed over a wide range, from 15–500 $\mu$m, using the same technique, but varying the orifice diameter, polymer solution flow rates and ultrasound frequency. The microspheres were hardened by solvent extraction/evaporation in an aqueous solution of 1% poly (vinyl alcohol). Aliquots of the microsphere suspension were placed on a microscope cover slip and imaged by light microscopy. The representative images shown in FIG. 2 illustrate the homogeneity of sphere diameters within a single preparation and the size range over which microspheres are obtained using this simple apparatus. The microspheres spontaneously assembled into hexagonal close-packed arrays; the hexagonal pattern and size uniformity extended over the entire sample on the cover slip.

The size distribution of the sphere populations was measured using a COULTER multisizer (BECKMAN INSTRUMENTS). As shown in FIGS. 3A and B, the distributions are very narrow. The peak width is similar to that of the commercial size standard used to calibrate the instrument. FIG. 3C demonstrates the ability to manipulate size distributions by instantaneously stepping up the flow rate and shifting down the acoustic frequency mid-way through the experiment, causing the particle diameter to shift from 73 to 82 $\mu$m. To generate the distribution shown in FIG. 3D, the flow rates were manually increased and the acoustic frequency decreased, maintaining each set of conditions for decreasing times. Because the parameters were varied manually, the distribution is not smooth, but it nevertheless shows that pre-defined microsphere size distributions, can in fact be generate.

Example 2

Preparing PLGA of Smaller Sphere Size

The minimum sphere diameter obtainable with this basic technique is governed by the size of the nozzle. Decreasing the orifice size beyond ~30 $\mu$m is problematic for several reasons. First, reproducible fabrication of the nozzles, by pulling capillaries for example, is increasingly difficult as the size decreases. Second, very small nozzles are easily clogged by aggregated polymer or foreign dust particles, and careful washing of all equipment and filtering of solutions is required. These are simply technical problems that could be overcome with careful engineering of the system. A confounding problem, however, is that passing the viscous polymer solutions through the small orifices becomes increasingly difficult and generates larger shear forces as the orifice diameter is decreased. Thus, the electrohydrodynamic spraying technique has been explored to produce microspheres less than about 30 $\mu$m in diameter.

Figure 4:
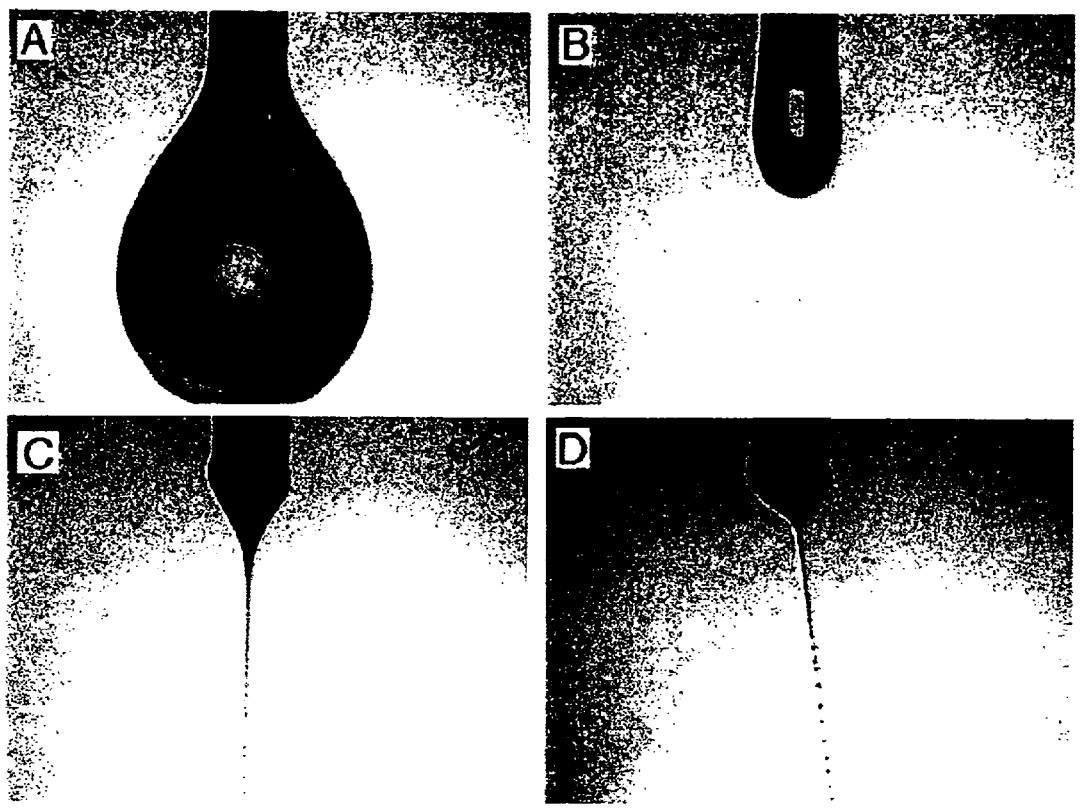
FIG. 4 demonstrates that the electrohydrodynamic apparatus reduces the size of PLGA/ethyl acetate particles.

The electrohydrodynamic apparatus reduces the size of PLGA particles. In these preliminary experiments, a PLGA/ acetone solution was passed through an 800 $\mu$m nozzle. As shown in FIG. 4A, in the absence of an applied charge, the drops exiting the nozzle were several millimeters in diameter, approximately four times the nozzle diameter. As an increasing potential to the nozzle was applied, however, the drop size quickly decreased, ultimately resulting in PLGA particles of ~10 $\mu$m diameter (FIGS. 4B–D). Further increase in the electrical charge generated the "multi-jet mode" of particle spraying in which the polymer solution was ejected in a fine mist and the individual particles were too small to be observed using our existing imaging apparatus.

Figure 5:
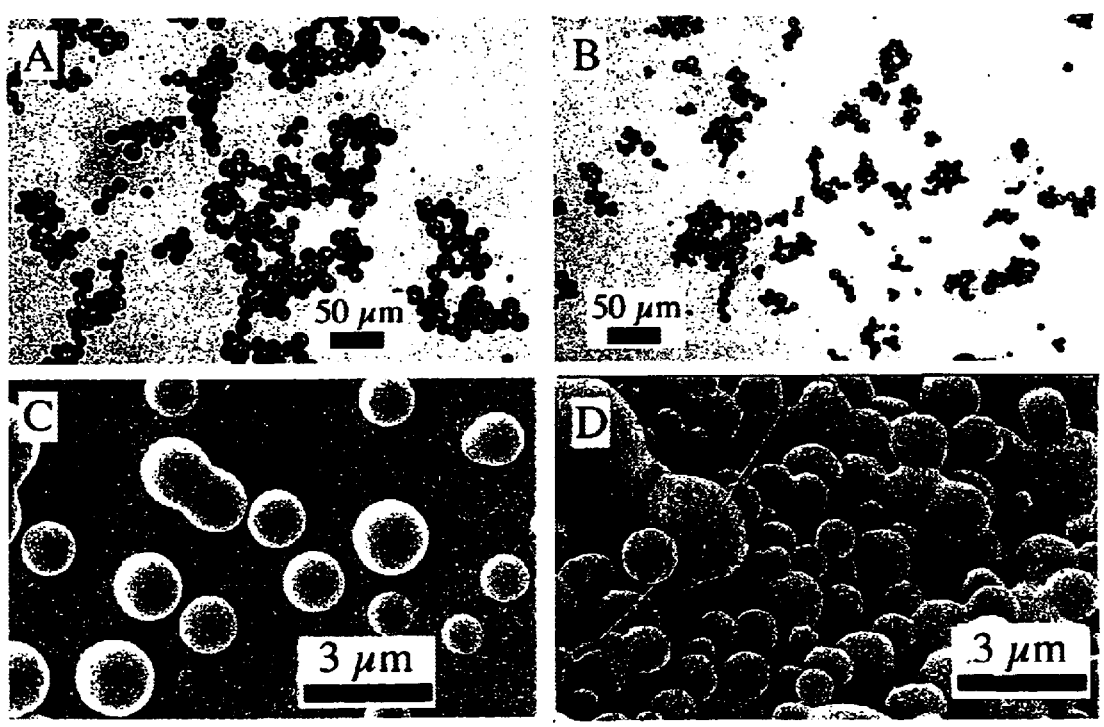
FIGS. 5A and B demonstrate the small sphere size obtainable even with crude, non-optimized apparatus.
FIGS. 5C and D demonstrate collected smaller spheres from 3 µm down.

To demonstrate the small sphere size obtainable even with our crude, non-optimized apparatus, PLGA particles were generated from a smaller (100 $\mu$m) glass nozzle using the electrohydrodynamic technique. The particles were collected by two different methods. Spheres ~3–30 $\mu$m in diameter were collected by allowing them to fall into a bath of liquid nitrogen, where the spheres froze, and subsequently extracting the solvent in cold ethanol. Spheres of approximately 10 and 5 $\mu$m in diameter are illustrated in FIGS. 5A and B, respectively. Smaller spheres from 3 $\mu$m down to 100 nm in diameter were collected, on a silicon EM stub placed beneath the stream and subsequently imaged by SEM (FIGS. 5C and D). Because the spheres were captured after only minimal drying time during their fall to the stub, the spheres were not individually isolated. Rather, the polymer/ solvent droplets tended to aggregate on the silicon surface. The particle size and spherical shape is nevertheless apparent in this image. Most importantly, the spheres are approximately 1 $\mu$m in diameter with a significant fraction of spheres in the nanometer range. Furthermore, acoustic excitation was not employed in this experiment, and the resulting spheres are not completely homogeneous. The size distribution nevertheless appears rather uniform. As these spheres were fabricated with a relatively large nozzle and primitive experimental set-up, there is little doubt that it will be possible to consistently generate submicron spheres using a more refined version of this technique.

Example 3

Encapsulation of Drugs

Figure 6:
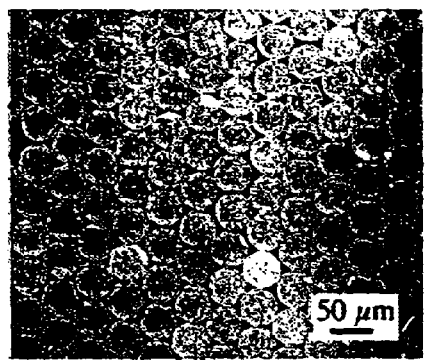
FIG. 6 demonstrates the ability to encapsulate drugs within the polymer microspheres using a model compound, rhodamine B, via fluorescence microscopy.
Figure 6:
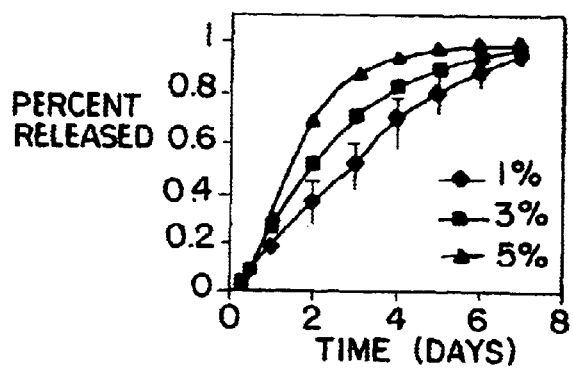

Finally, the ability to encapsulate drugs within the polymer microspheres using a model compound, rhodamine B has been demonstrated. The rhodamine B, in its free base form, was dissolved in PLGA/ethyl acetate solutions at theoretical loadings of 1, 3 and 5%(mass drug/mass polymer). Microspheres of uniform 35, 50 and 65 $\mu$m diameters were fabricated, hardened and collected using the procedures described in the above examples. The presence of rhodamine had no observable effect on particle uniformity. Encapsulation of rhodamine (~70% efficiency) was confirmed by fluorescence microscopy (FIG. 6, right). The rhodamine B is released from the spheres over the course of 7–10 days of incubation in PBS and 37° C. The release rate was faster when spheres were smaller (not shown) or contained more drug (FIG. 6, left) as would be expected.

Example 4

Fabrication of PLG Polymer Shells Containing an Oil Core

A dual nozzle system having an inner nozzle (100 $\mu$m orifice) carrying a core material and an "outer" nozzle (250 $\mu$m orifice) carrying a shell material was oriented inside a third nozzle generating a stream of non-solvent for the acceleration of the core/shell stream. In this case, canola oil was pumped through the inner nozzle. PLG was dissolved in methylene chloride (50 mg/mL) and pumped through the "outer" nozzle carrying shell material. A small amount of rhodamine B (~1%) was dissolved in the PLG phase in some instances for imaging the shell of the particles and to demonstrate the ability to encapsulate a model drug. A solution of 1% (wt/wt) PVA in water flowed from the third nozzle around the core/shell stream to narrow this stream and to facilitate the entry of the resulting particles into an aqueous, non-solvent bath for methylene chloride extraction and particle hardening. The nozzle was acoustically excited at various frequencies depending on the particle size desired (0–50 kHz).

Overall particle size, shell thickness and core radius were manipulated independently. By varying the velocity of the 1% PVA stream, the overall diameter of individual particles was adjusted. Increasing the velocity of the 1% PVA stream causes an acceleration of the core and shell streams resulting in a decrease in overall particle size. Further adjustment of overall particle size was possible by changing the acoustic excitation frequency as described in Example 1, and both parameters (namely, the velocity of the 1% PVA stream and the acoustic excitation frequency) were adjusted to achieve a desired particle size. Also, by careful adjustment of the oil (core) and PLG (shell) stream flow rates, particles having various core radii or shell thickness were obtained. Changing the PLG stream flow rate produced shells having a consistent core radius and varying, controlled shell thickness. Changing the oil stream flow rate while holding other parameters constant produced shells having a consistent shell volume and a controlled core radius. In this way, it is possible to fabricate core/shell particles exhibiting controllable and well defined overall size and ratio of shell thickness to core radius. In this case, by modulating the relative flow rates of the streams as well as the acoustic excitation frequency, uniform particles were produced ranging from 20 to 70 $\mu$m in diameter having a controlled and uniform shell thickness over a range of 3 to 35 $\mu$m.

Figure 3:
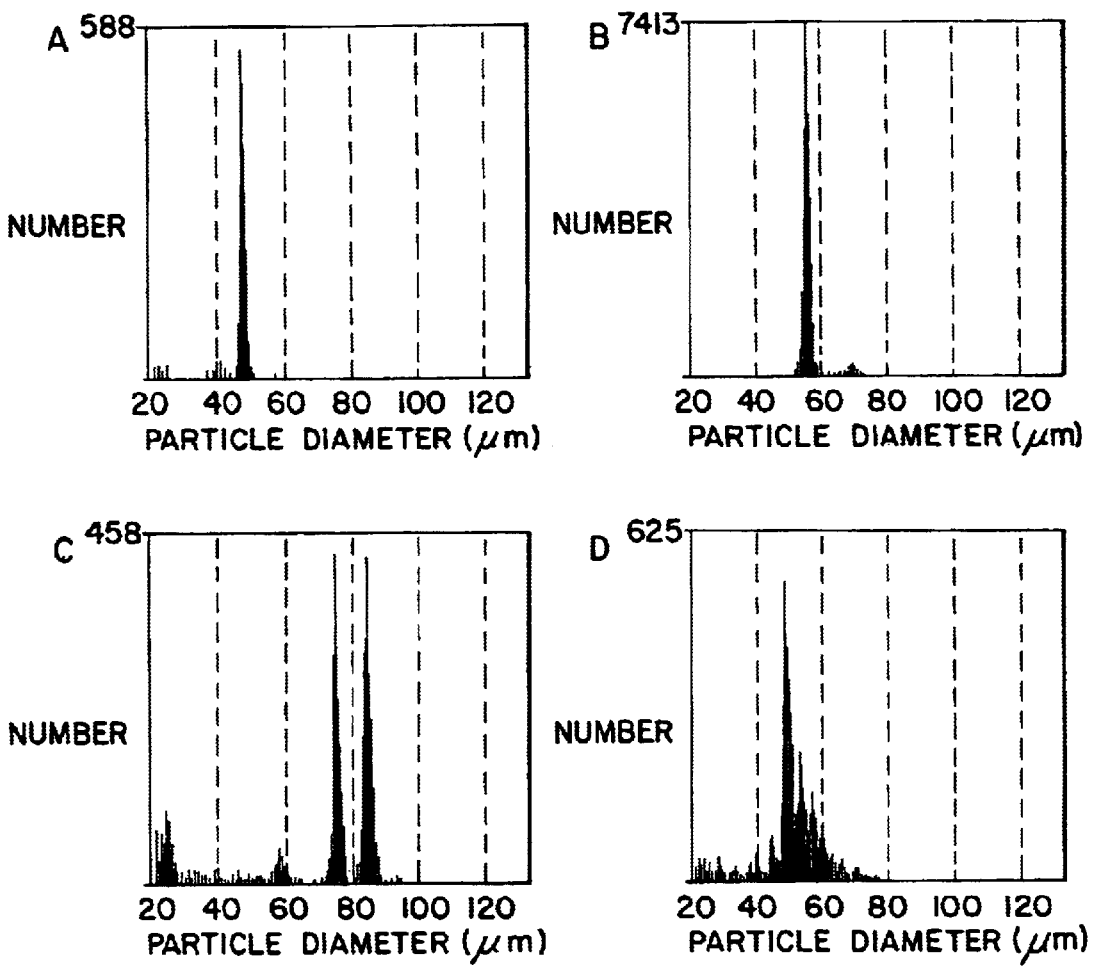
FIGS. 3A and B show the size distribution of sphere populations measured using a COULTER multisizer.
FIG. 3C demonstrates the ability to manipulate size distributions by instantaneously changing the flow rate and acoustic frequency.
FIG. 3D demonstrates the ability to generate continuously varying size distributions.

Particle size distribution and aspect ratio were verified by optical microscopy and by fluorescent detection of the encapsulated rhodamine B. Size distributions were found to be comparable to distributions obtained when producing solid particles (FIG. 3). Also, particles had a consistent and uniform shell thickness and core radius across a given sample as verified by optical cross-sectioning using confocal fluorescence microscopy.

Thus, it is apparent that there has been provided, in accordance with the instant invention, a process that fully satisfies the objects and advantages set forth herein above. While the invention has been described with respect to various specific examples and embodiments thereof, it is understood that the invention is not limited thereto and many alternatives, modifications and variations will be apparent to those skilled in the art in light of the foregoing description. Accordingly, it is intended to embrace all such alternatives, modifications and variations as fall within the spirit and broad scope of the invention.

What is claimed is:

1. A method of forming particles, comprising:
   accelerating a first stream comprising a first liquid; and
   vibrating the first stream, to form particles;
   wherein the particles have an average diameter of at most 100 $\mu$m.

2. The method of claim 1, further comprising solidifying the particles.

3. The method of claim 1, wherein the particles comprise a core and a shell.

4. The method of claim 3, wherein the particles comprise a plurality of shells.

5. The method of claim 1, wherein the particles comprise a pharmaceutical composition.

6. The method of claim 3, wherein the core comprises a pharmaceutical composition.

7. The method of claim 1, wherein the accelerating comprises contacting the first stream with a second stream, and
   the second stream comprises a second liquid.

8. The method of claim 7, wherein the second stream surrounds the first stream.

9. The method of claim 1, wherein the accelerating comprises applying charge to the first stream.

10. The method of claim 9, wherein
    a second stream comprising a second liquid surrounding the first stream, and
    the accelerating further comprises accelerating the second stream.

11. The method of claim 10, wherein the particles comprise a core and a shell.

12. The method of claim 11, wherein the particles comprise a plurality of shells.

13. The method of claim 1, further comprising forming the first stream by passing the first liquid through a nozzle.

14. The method of claim 13, wherein the nozzle has a diameter greater than ½ an average diameter of the particles.

15. The method of claim 14, wherein the nozzle has a diameter at least the average diameter.

16. The method of claim 1, wherein the particles have an average diameter of at most 50 $\mu$m.

17. The method of claim 16, wherein the particles have an average diameter of 10 nm to 50 $\mu$m.

18. The method of claim 16, wherein the particles have an average diameter of 1 $\mu$m to 50 $\mu$m.

19. The method of claim 1, wherein the particles have an average diameter of 50 to 100 $\Xi$m, and 90% of the particles have a diameter that is within 2% of an average diameter of the particles.

20. The method of claim 1, wherein the particles have an average diameter of 1 to 50 $\mu$m, and 90% of the particles have a diameter that is within 1 $\mu$m of an average diameter of the particles.

21. The method of claim 1, wherein
    the accelerating is a step for accelerating the first stream, and
    the vibrating is a step for vibrating the first stream.

22. A method of forming particles, comprising:
    accelerating a first stream comprising a first liquid;
    wherein the accelerating comprises applying charge to the first stream, and
    the particles comprise a core and a shell.

23. The method of claim 22, further comprising solidifying the particles.

24. The method of claim 22, wherein the particles comprise a plurality of shells.

25. The method of claim 22, wherein the particles comprise a pharmaceutical composition.

26. The method of claim 22, further comprising forming the first stream by passing the first liquid through a nozzle, and
    wherein the nozzle has a diameter at least ½ the average diameter of the particles.

27. The method of claim 22, wherein the particles have an average diameter of at most 100 $\mu$m.

28. The method of claim 22, wherein the particles have an average diameter of 10 nm to 50 µm.

29. Particles, prepared by the method of claim 19.

30. Particles, prepared by the method of claim 20.

31. A method of forming particles, comprising:

accelerating a first stream comprising a first liquid into a surrounding liquid; and vibrating the first stream, to form particles.

32. The method of claim 31, further comprising solidifying the particles.

33. The method of claim 31, wherein the particles comprise a core and a shell.

34. The method of claim 33, wherein the particles comprise a plurality of shells.

35. The method of claim 31, wherein the particles comprise a pharmaceutical composition.

36. The method of claim 33, wherein the core comprises a pharmaceutical composition.

37. The method of claim 31, wherein the accelerating comprises contacting the first stream with a second stream, and the second stream comprises a second liquid.

38. The method of claim 32, wherein the second stream surrounds the first stream.

39. The method of claim 31, wherein the accelerating comprises applying charge to the first stream.

40. The method of claim 39, wherein a second stream comprising a second liquid surrounding the first stream, and the accelerating further comprises accelerating the second stream.

41. The method of claim 40, wherein the particles comprise a core and a shell.

42. The method of claim 41, wherein the particles comprise a plurality of shells.

43. The method of claim 31, further comprising forming the first stream by passing the first liquid through a nozzle.

44. The method of claim 43, wherein the nozzle has a diameter greater than ½ an average diameter of the particles.

45. The method of claim 44, wherein the nozzle has a diameter at least the average diameter of the particles.

46. The method of claim 31, wherein the particles have an average diameter of at most 100 µm.

47. The method of claim 31, wherein the particles have an average diameter of at most 50 µm.

48. The method of claim 47, wherein the particles have an average diameter of 10 nm to 50 µm.

49. The method of claim 48, wherein the particles have an average diameter of 1 µm to 50 µm.

50. The method of claim 31, wherein the particles have an average diameter of 50 to 100 µm, and 90% of the particles have a diameter that is within 2% of an average diameter of the particles.

51. The method of claim 31, wherein the particles have an average diameter of 1 to 50 µm, and 90% of the particles have a diameter that is within 1 µm of an average diameter of the particles.

52. The method of claim 31, wherein the accelerating is a step for accelerating the first stream, and the vibrating is a step for vibrating the first stream.

53. A method of forming particles, comprising:

accelerating a first stream comprising a first liquid into a surrounding liquid;

wherein the accelerating comprises applying charge to the first stream, and the particles comprise a core and a shell.

54. The method of claim 53, further comprising solidifying the particles.

55. The method of claim 53, wherein the particles comprise a plurality of shells.

56. The method of claim 53, wherein the particles comprise a pharmaceutical composition.

57. The method of claim 53, further comprising forming the first stream by passing the first liquid through a nozzle, and wherein the nozzle has a diameter at least ½ the average diameter of the particles.

58. The method of claim 53, wherein the particles have an average diameter of at most 100 µm.

59. The method of claim 53, wherein the particles have an average diameter of 10 nm to 50 µm.

* * * * *

UNITED STATES PATENT AND TRADEMARK OFFICE
CERTIFICATE OF CORRECTION

PATENT NO. : 6,669,961 B2
APPLICATION NO. : 09/931640
DATED : August 15, 2001
INVENTOR(S) : Kyekyoon Kim et al.

It is certified that error appears in the above-identified patent and that said Letters Patent is hereby corrected as shown below:

In the claims:
Col. 20, Line 39 in claim 19, please delete "ΞM" and insert --µm--.
Col. 21, Line 23 in claim 38, please delete "32" and insert --37--.
Col. 22, Line 5 in claim 49, please delete "48" and insert --47--.

Signed and Sealed this

Twenty-ninth Day of May, 2007

JON W. DUDAS
*Director of the United States Patent and Trademark Office*

UNITED STATES PATENT AND TRADEMARK OFFICE
CERTIFICATE OF CORRECTION

PATENT NO. : 6,669,961 B2
APPLICATION NO. : 09/931640
DATED : December 30, 2003
INVENTOR(S) : Kyekyoon Kim et al.

It is certified that error appears in the above-identified patent and that said Letters Patent is hereby corrected as shown below:

In the claims:
Col. 20, Line 39 in claim 19, please delete "ΞM" and insert --μm--.
Col. 21, Line 23 in claim 38, please delete "32" and insert --37--.
Col. 22, Line 5 in claim 49, please delete "48" and insert --47--.

This certificate supersedes Certificate of Correction issued May 29, 2007.

Signed and Sealed this

Tenth Day of July, 2007

JON W. DUDAS
*Director of the United States Patent and Trademark Office*